United States Patent
Hoke et al.

(10) Patent No.: US 9,527,817 B2
(45) Date of Patent: Dec. 27, 2016

(54) COMPOUNDS FOR TREATING PERIPHERAL; NEUROPATHIES AND OTHER NEURODEGENERATIVE; DISORDERS

(75) Inventors: Ahmet Hoke, Towson, MD (US); Weiran Chen, Columbia, MD (US); Jing Zhu, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/127,326

(22) PCT Filed: Jun. 21, 2012

(86) PCT No.: PCT/US2012/043475
§ 371 (c)(1),
(2), (4) Date: Jun. 17, 2014

(87) PCT Pub. No.: WO2012/177831
PCT Pub. Date: Dec. 27, 2012

(65) Prior Publication Data
US 2014/0303203 A1   Oct. 9, 2014

Related U.S. Application Data

(60) Provisional application No. 61/499,242, filed on Jun. 21, 2011, provisional application No. 61/499,921, filed on Jun. 22, 2011.

(51) Int. Cl.
| | | |
|---|---|---|
| *C07D 215/48* | (2006.01) | |
| *A61K 31/47* | (2006.01) | |
| *C07D 215/20* | (2006.01) | |
| *C12Q 1/34* | (2006.01) | |
| *G01N 33/50* | (2006.01) | |

(52) U.S. Cl.
CPC ............ *C07D 215/48* (2013.01); *A61K 31/47* (2013.01); *C07D 215/20* (2013.01); *C12Q 1/34* (2013.01); *G01N 33/5008* (2013.01)

(58) Field of Classification Search
CPC ...... C07D 215/20; C07D 215/48; A61K 31/47
USPC .......................................... 546/159; 514/312
See application file for complete search history.

(56) References Cited

U.S. PATENT DOCUMENTS

| | | |
|---|---|---|
| 3,952,023 A | 4/1976 | Kaiya et al. |
| 4,196,113 A | 4/1980 | Kaiya et al. |
| 6,746,678 B1 | 6/2004 | Shapiro |
| 2005/0137146 A1 | 6/2005 | Landers |
| 2007/0078144 A1 | 4/2007 | Stockwell |
| 2009/0179638 A1 | 7/2009 | Barker et al. |
| 2010/0105630 A1 | 4/2010 | Blagg |
| 2010/0279311 A1 | 11/2010 | Kimura |

FOREIGN PATENT DOCUMENTS

WO   0068693 A2   11/2000

OTHER PUBLICATIONS

Mecocci, Blochimica et Biophysica Acta 1822, (2012) pp. 631-638.*
Gilgun-Sherki, Neuropharmacology vol. 40, (2001) p. 959-975.*
Skaare, Xenobiotica, 1979, vol. 9(11), p. 649-657.*
Fentsov, CA 112:234619, abstract only of Neftekhimiya, (1990), Voi 30(1), p. 103-108.*
Taimr, Die Angewandte Markomolekulare Chemie, Voi 217, (1994), p. 119-128 (Nr. 3796).*
Thorisson, JAOCS, vol. 69, No. 8, Aug. 1992, p. 806-809.*
Sreedhar, J Biol Chem, 2003, 278:35231-35240.*
Wikipedia.org website, search term "antioxidants", May 8, 2015, pp. 1-22.*
Wolf, E J of Cancer, Voi 44, 1507-1515, 2008.*
Tal, abstract only of Neuroreport, 7(8), 1382-1384, May 1996.*
Lakshmi Galam et al., "High-throughput assay for the identification of Hsp90 inhibitors based on Hsp90-dependent refolding of firefly luciferase", Bioorganic & Medicinal Chemistry, vol. 15, No. 5, pp. 1939-1946, 2007.
International Search Report dated Jan. 2, 2013 from PCT International Application No. PCT/US2012/043475.
Keswani et al., "FK506 is neuroprotective in a model of antiretroviral toxic neuropathy," Annals of Neurology, 53(1 ):57-64 (2003).
Rowlands et al., "High-throughput screening assay for inhibitors of heat-shock protein 90 ATPase activity", Analytical Biochemistry, vol. 327, pp. 176-183, 2004.
Taimr et al., Antioxidants and stabilizers, CXIII. Oxidation products of the antidegradant ethoxyquin, Die Angewandte Makromolekulare Chemie, vol. 190, pp. 53-65, 1991.
European Search Report dated Jan. 22, 2015 from European Application No. EP12802536.
Dorey G et al: "New quinolinic derivatives as centrally active antioxidants" Bioorganic & Medicinal Chemistry Letters, Pergamon, Amsterdam, NL, vol. 10, No. 9, May 1, 2000 (May 1, 2000), pp. 935-939.
Hanig J P et al: "Protection with butylated hydroxytoluene and other compounds against intoxication and mortality caused by hexachlorophene", Food and Chemical Toxicology, Pergamon, GB, vol. 22, No. 3, Mar. 1, 1984 (Mar. 1, 1984), pp. 185-189.
Plumb G W et al: "Effect of Ethoxyquin on Glutathione Levels and Peroxidisability of Rat Liver Membranes", Biochemical Society Transactions, Portland Press Ltd, GB, vol . 24, No. 3, Jan. 1, 1996 (Jan. 1, 1996), p. 380S.

(Continued)

*Primary Examiner* — D M Seaman
(74) *Attorney, Agent, or Firm* — Ward and Smith, P.A.; Jeffrey W. Childers

(57) ABSTRACT

Compounds and methods for treating or preventing a neurodegenerative disease, disorder or condition associated with the overall activity of hsp90 but not with the ATPase activity of hsp90, including peripheral neuropathy, such as peripheral neuropathy caused by chemotherapy or diabetes, disorders 5 of the central nervous system, such as Alzheimer's disease and Parkinsons disease, and motor neuron diseases, such as amyotrophic lateral sclerosis (ALS), in a subject are provided.

3 Claims, 11 Drawing Sheets

(56) References Cited

OTHER PUBLICATIONS

Adachi H et al: "Heat shock proteins in neurodegenerative diseases: pathogenic roles and therapeutic implications", International Journal of Hyperthermia, Basingstoke, GB, vol. 25, No. 8, Dec. 1, 2009 (Dec. 1, 2009), pp. 647-654.
Mariani E et al: "Oxidative stress in brain aging, neurodegenerative and vascular diseases: An overview", Journal of Chromatography B: Biomedical Sciences & Applications, Elsevier, Amsterdam, NL, vol. 827, No. 1, Nov. 15, 2005 (Nov. 15, 2005), pp. 65-75.
Lewis et al. "High-Dosage Ascorbic Acid Treatment in Charcot-Marie-Tooth Disease Type 1A: Results of a Randomized, Double-Masked, Controlled Trial", JAMA Neurol., Aug. 1, 2013; 70(8): 981-987.
Chen, W.; Mi, R.; Haughey, N.; Oz, M; Hoke, A., "Immortalization and characterization of a nociceptive dorsal root ganglion sensory neuronal line," J Peripher. Nerv. Syst. 12(2), 121-130 (2007).
Koul et al., "Diarylquinolines Target Subunit C ofMycobacterial ATP Synthase," Nature Chemical Biology 3:323-324 (2007).
Hoke et al., "Schwann Cells Express Motor and Sensory Phenotypes That Regulate Axon Regeneration," J Neurosci. 26(38):9646-9655 (2006).
Höke and Ray, "Rodent Models of Chemotherapy-Induced Peripheral Neuropathy", ILAR Journal, vol. 54, No. 3, p. 273-281, 2014.

\* cited by examiner

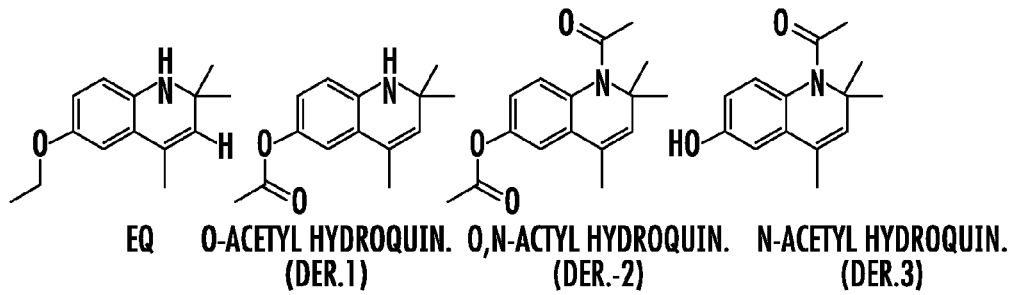

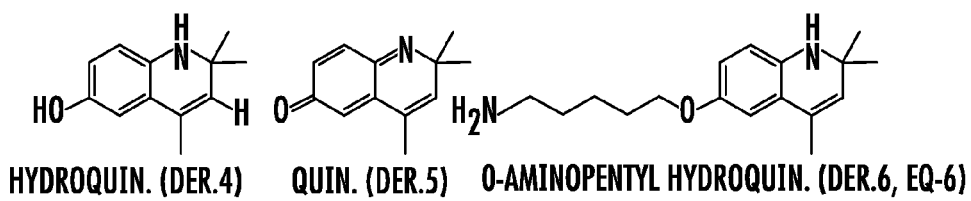

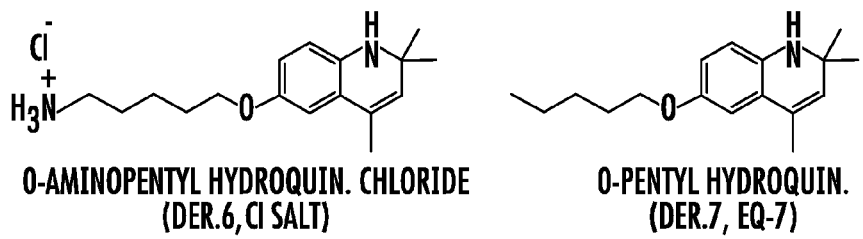

| | |
|---|---|
| EQ | 6-ETHOXY-2,2,4-TRIMETHYL-1,2-DIHYDROQUINOLINE |
| O-ACETYL HYDROQUIN. | 2,2,4-TRIMETHYL-1,2-DIHYDROQUINOLINE-6-YL ACETATE |
| O,N-ACTYL HYDROQUIN. | 1-ACETYL-2,2,4-TRIMETHYL-1,2-DIHYDROQUINOLINE-6-YL ACETATE |
| N-ACETYL HYDROQUIN. | 1-ACETYL-2,2,4-TRIMETHYL-1,2-DIHYDROQUINOLINE-6-OL |
| HYDROQUIN. | 2,2,4-TRIMETHYL-1,2-DIHYDRO-6-QUINOLINOL |
| QUIN. | 2,6-DIHYDRO-2,2,4-TRIMETHYL-6-QUINOLINE |
| O-AMINOPENTYL HYDROQUIN. | 6-(5-AMINO)-PENTOXY-2,2,4-TRIMETHYL-1,2-DIHYDROQUINOLINE |
| O-PENTYL HYDROQUIN. | 6-PENTOXY-2,2,4-TRIMETHYL-1,2-DIHYDROQUINOLINE |
| O-AMINOPENTYL HYDROQUIN. CHLORIDE | 6-(2-AMINO)-ETHOXY-2,2,4-TRIMETHYL-1,2-DIHYDROQUINOLINE CHLORIDE |

*FIG. 1*

POTENCY OF ETHOXYQUIN AND IT'S DERIVATIVES AGAINST PTX NEUROTOXICITY

ETHOXYQUIN   100% NP AT 300nM
DER. 1       85% NP AT 10nM
DER. 2       82% NP AT 60nM
DER. 3       70% NP AT 70nM
DER. 4       100% NP AT 70nM
DER. 5       96% NP AT 300nM
DER. 7       94% NP AT 30nM

FIG. 3

COMPOUNDS FOR TREATING PERIPHERAL; NEUROPATHIES AND OTHER NEURODEGENERATIVE; DISORDERS

REFERENCE TO RELATED APPLICATIONS

This application is a 35 U.S.C. § 371 U.S. national phase entry of International Application No. PCT/US2012/043475 having an international filing date of Jun. 21, 2012, which claims the benefit of U.S. Provisional Application No. 61/499,242, filed Jun. 21,2011, and also claims the benefit of U.S. Provisional Application No. 61,499,921, file Jun. 22, 2011, the content of each of the aforementioned applications is herein incorporated by reference in its entirety.

BACKGROUND

Neurodegenerative disorders affect many people worldwide. These disorders include peripheral neuropathies, which are a group of neurodegenerative disorders affecting the peripheral nerves, such as peripheral neuropathy caused by chemotherapy or diabetes; disorders of the central nervous system, such as Alzheimer's disease and Parkinson's disease; and motor neuron diseases, such as amyotrophic lateral sclerosis (ALS). Currently, no effective therapy for preventing nerve degeneration exists, except in cases of autoimmune peripheral neuropathies.

Heat shock proteins are a class of functionally related proteins involved in the folding and unfolding of other proteins. They play an important role in the cell under normal conditions and also are a primary part of the heat shock response. They make up approximately 1% to 2% of total protein in unstressed cells. This percentage increases to 4% to 6% of total protein in cells that are stressed, such as during elevated temperatures, inflammation, or infection.

Heat shock proteins have several important functions in a cell under normal conditions. One function is to act as intracellular chaperones for other proteins. By helping to stabilize partially unfolded proteins, heat shock proteins aid in transporting proteins across membranes within a cell. They also play an important role in other protein-protein interactions, such as protein folding, assisting in the establishment of proper protein conformation, preventing unwanted protein aggregation, and carrying old proteins destined for degradation to a proteasome in the cell.

Heat shock proteins, however, also can assist in promoting diseases or disorders. For example, heat shock proteins can aid in the correct functioning of tumor promoting proteins, such as oncoproteins, and they have been found to be overexpressed in a range of cancers. They also may contribute to tumor cell survival by stabilizing aberrant signaling proteins and by interfering with apoptosis.

SUMMARY

In some aspects, the presently disclosed subject matter provides a method for treating, inhibiting, delaying, or preventing a neurodegenerative disorder in a subject, the method comprising administering to the subject a therapeutically effective amount of a compound of Formula (I) or Formula (II):

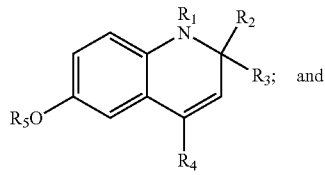

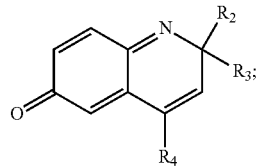

wherein: $R_1$ is selected from the group consisting of H, substituted or unsubstituted alkyl, and —C(=O)—$R_6$, wherein $R_6$ is substituted or unsubstituted alkyl; $R_2$, $R_3$, and $R_4$ are each independently substituted or unsubstituted alkyl; and $R_5$ is selected from the group consisting of H, substituted or unsubstituted alkyl, and —C(=O)—$R_6$; or a pharmaceutically acceptable salt thereof.

In particular aspects, the compound of Formula (I) or Formula (II) is selected from the group consisting of:

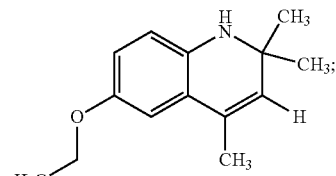

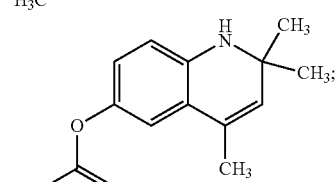

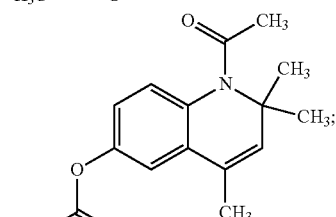

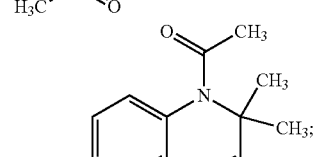

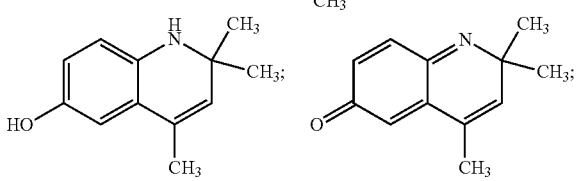

-continued

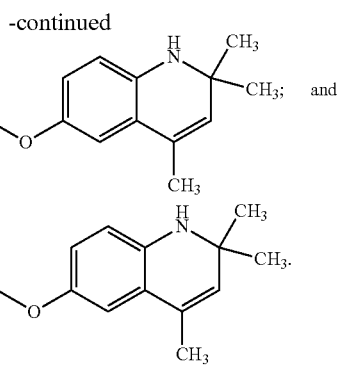

and

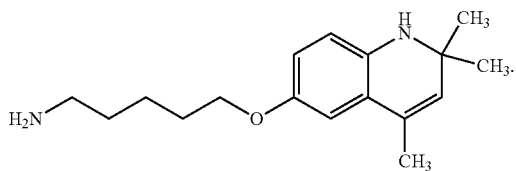 [SMILES: CC1=CC(C)(C)Nc2ccc(OCCCCCN)cc21]

In yet more particular aspects, the compound of Formula (I) is:

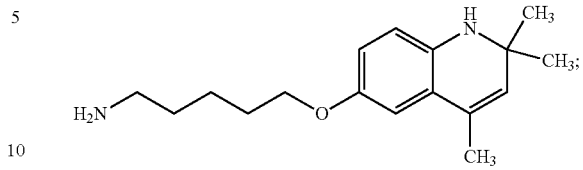

In some aspects, the neurodegenerative disorder comprises a peripheral neuropathy. In particular embodiments, the peripheral neuropathy is selected from the group consisting of a chemotherapy-induced peripheral neuropathy, a diabetes-induced peripheral neuropathy, an HIV-associated peripheral neuropathy, an idiopathic peripheral neuropathy, an alcohol-induced peripheral neuropathy, and a drug-induced peripheral neuropathy.

In other aspects, the neurodegenerative disorder is of the central nervous system. In some embodiments, the neurodegenerative disorder is selected from the group consisting of Alzheimer's disease, and Parkinson's disease. In yet other aspects, the neurodegenerative disorder comprises a motor neuron disease. In some embodiments, the motor neuron disease is amyotrophic lateral sclerosis (ALS).

In another aspect, the presently disclosed subject matter provides a method for modulating the overall activity of heat shock protein 90 (hsp90) without modulating the ATPase activity of hsp90 in a cell, the method comprising contacting the cell with a compound of Formula (I) or Formula (II), as defined hereinabove, in an amount sufficient to modulate the overall activity of hsp90 but not modulate the ATPase activity of hsp90.

In another aspect, the presently disclosed subject matter provides a method for screening for a neuroprotective compound that modulates the overall activity of hsp90, but does not modulate the ATPase activity of hsp90, the method comprising: contacting a cell having hsp90 overall activity with a candidate neuroprotective compound; contacting a cell that is inhibited for hsp90 overall activity with the candidate neuroprotective compound; adding a stress that can result in a neurodegenerative disorder to each cell; determining if the compound provides neuroprotection of the cell having hsp90 overall activity and does not provide neuroprotection of the cell which is inhibited for hsp90 overall activity; and determining the ATPase activity of hsp90 in the cell having hsp90 overall activity.

In yet another aspect, the presently disclosed subject matter provides a compound of the formula:

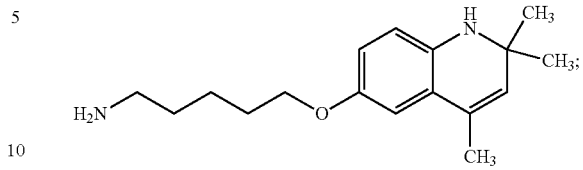

or a pharmaceutically acceptable salt thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 2A:
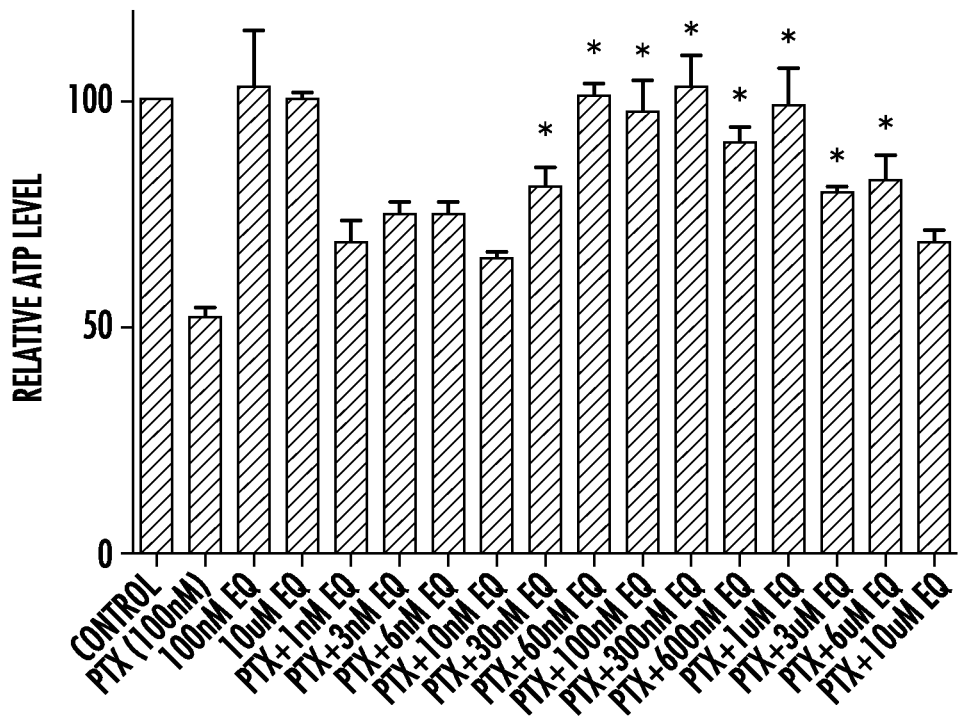
Figure 2B:
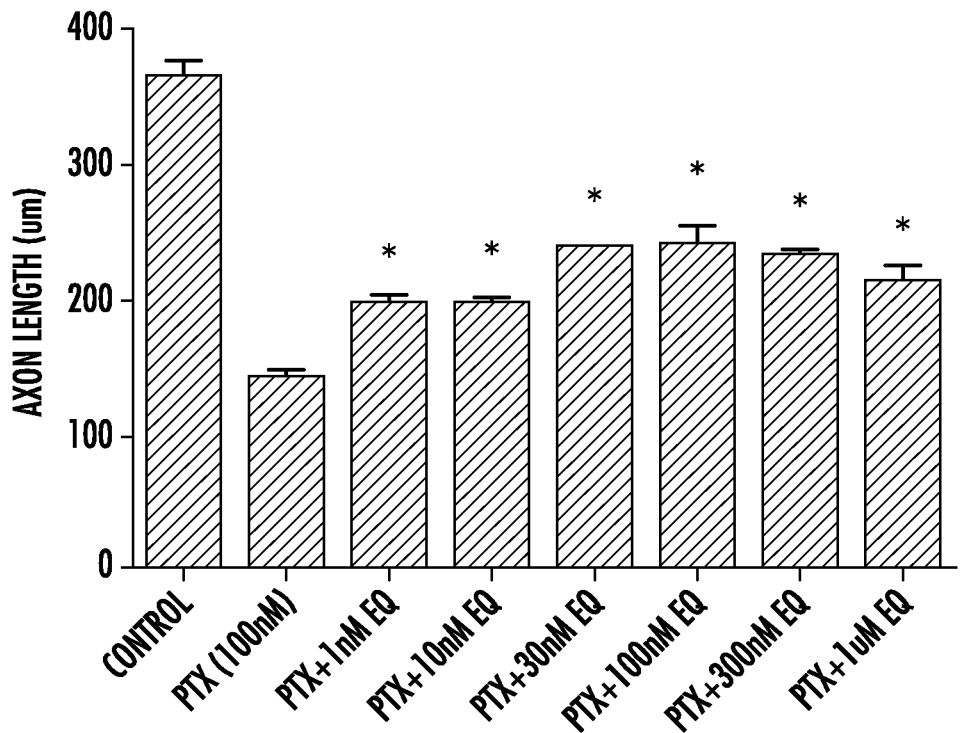

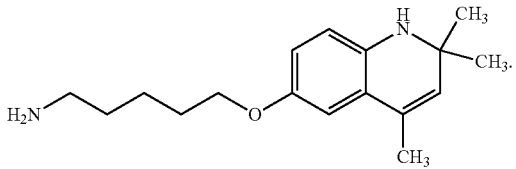 [SMILES: CC1=CC(C)(C)Nc2ccc(OCCCCCN)cc21]

3. The compound of claim 1, further comprising the chloride salt:
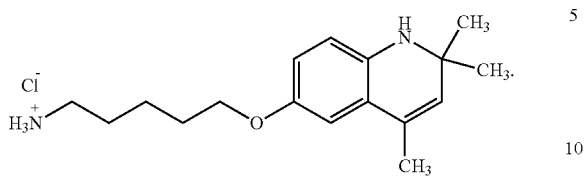

Having thus described the presently disclosed subject matter in general terms, reference will now be made to the accompanying Figures, which are not necessarily drawn to scale, and wherein:

FIG. 1 shows the chemical structure of EQ and representative derivatives (Der. 1-7);

FIGS. 2A and 2B show the ability of EQ to provide neuroprotection against paclitaxel (PTX) neurotoxicity in dorsal root ganglia (DRG) neuronal cells by measuring ATP levels (FIG. 2A) and axon lengths (FIG. 2B).

Figure 4:
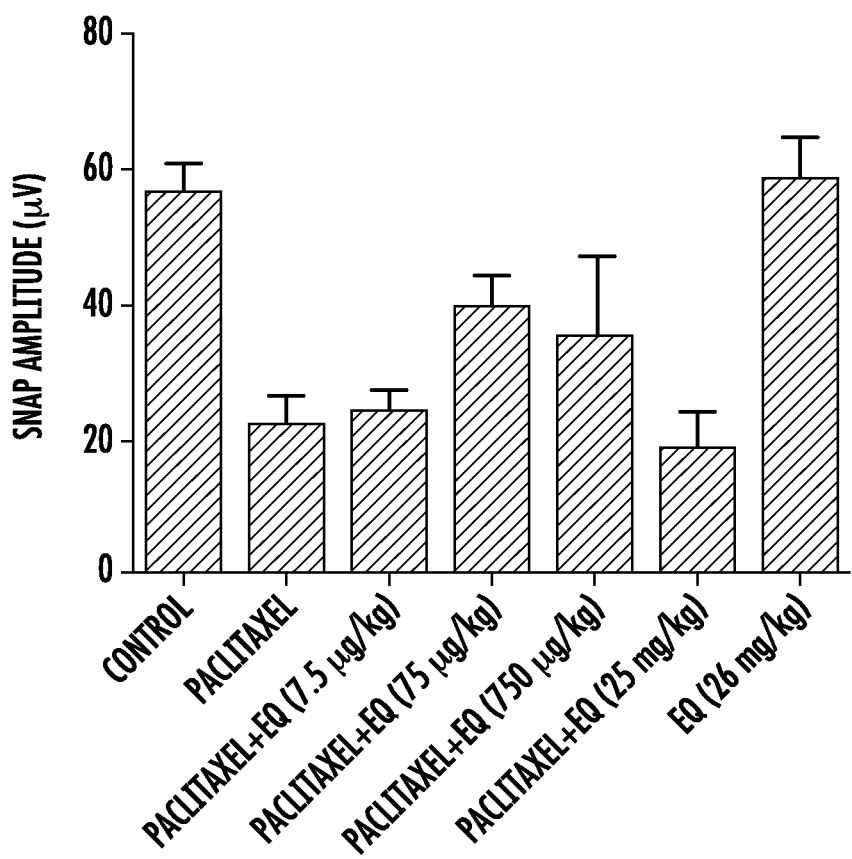
Figure 5:
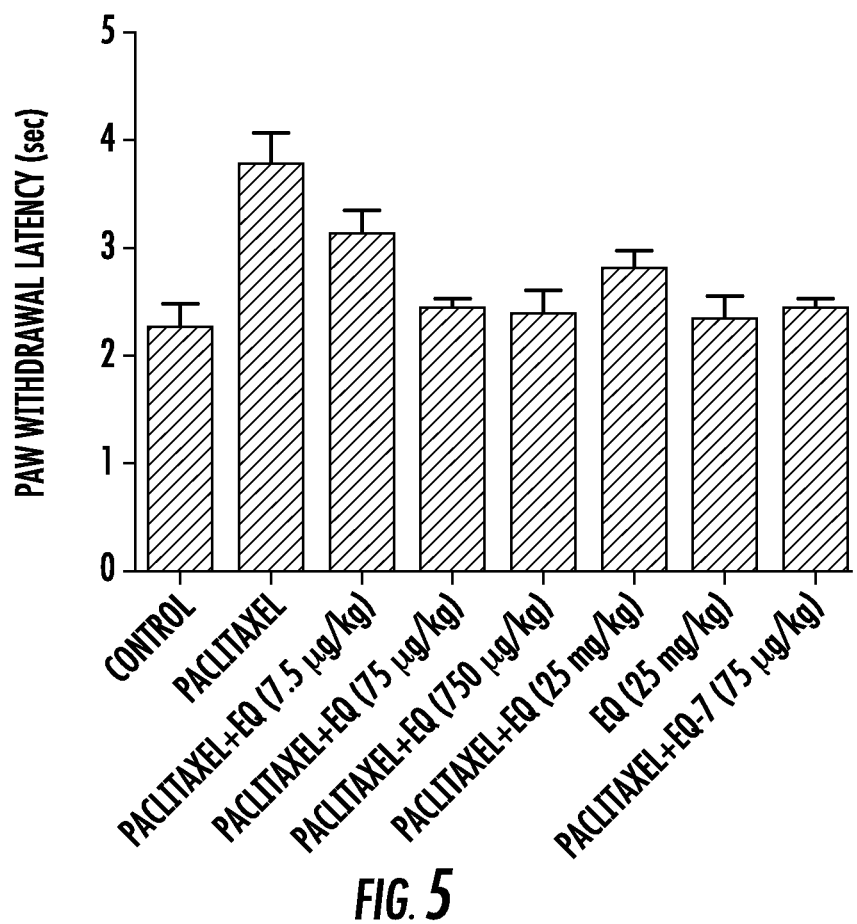
Figure 6:
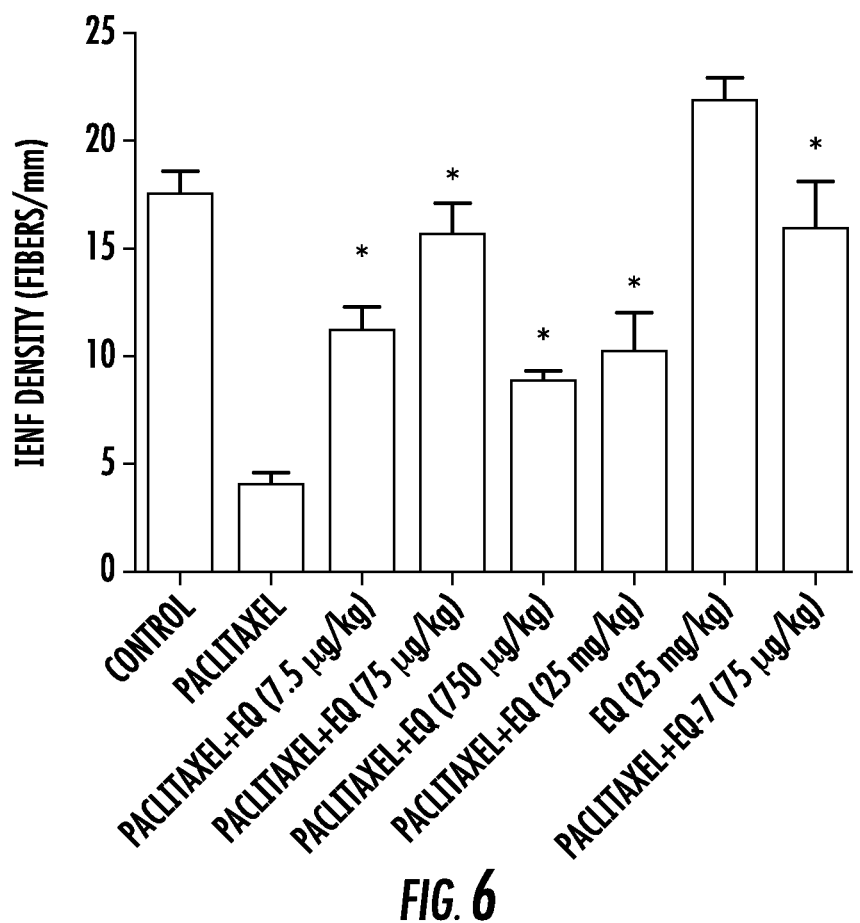
Figure 7:
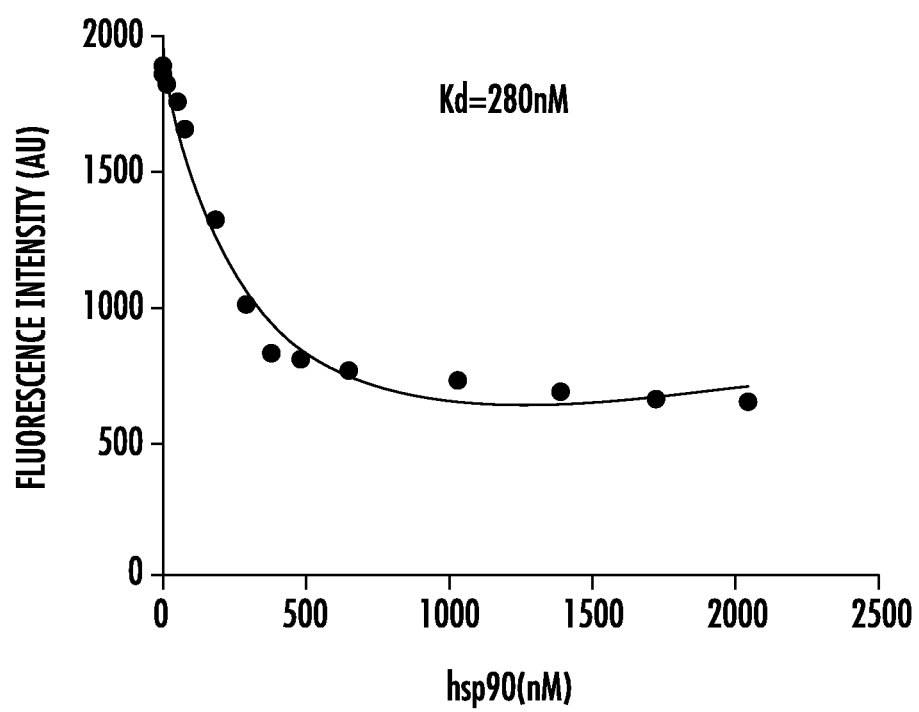
Figure 8:
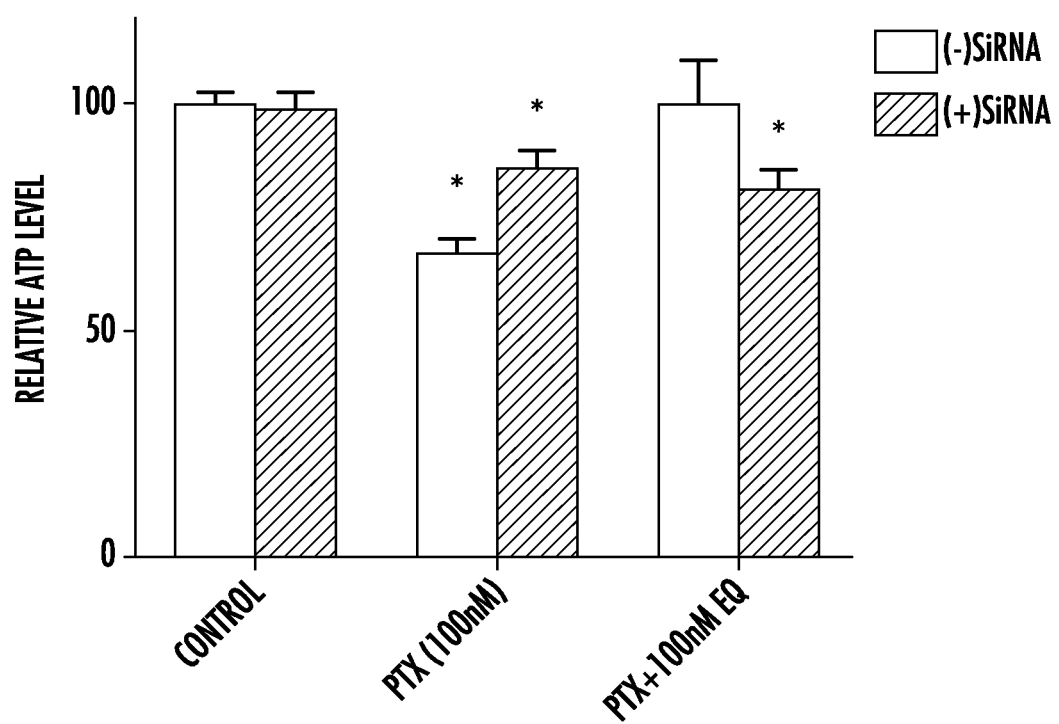
Figure 9:
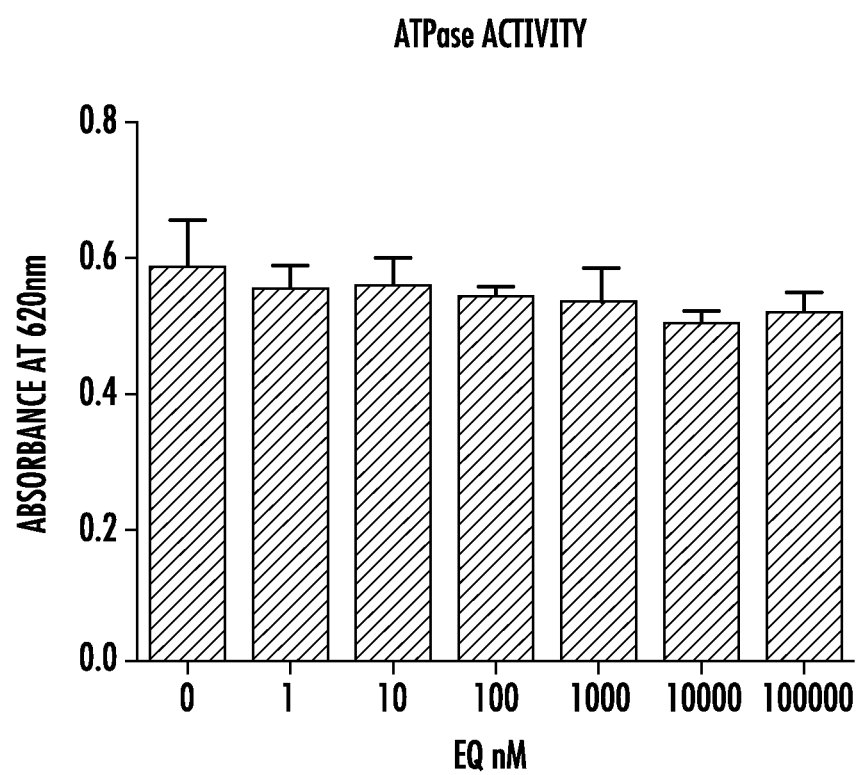
Figure 10:
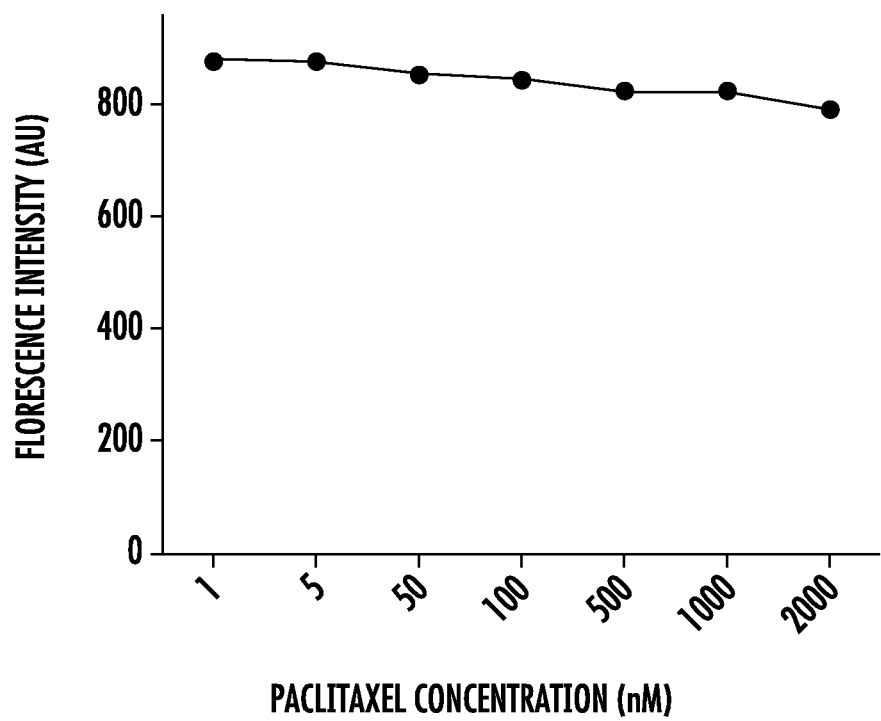
Figure 11:
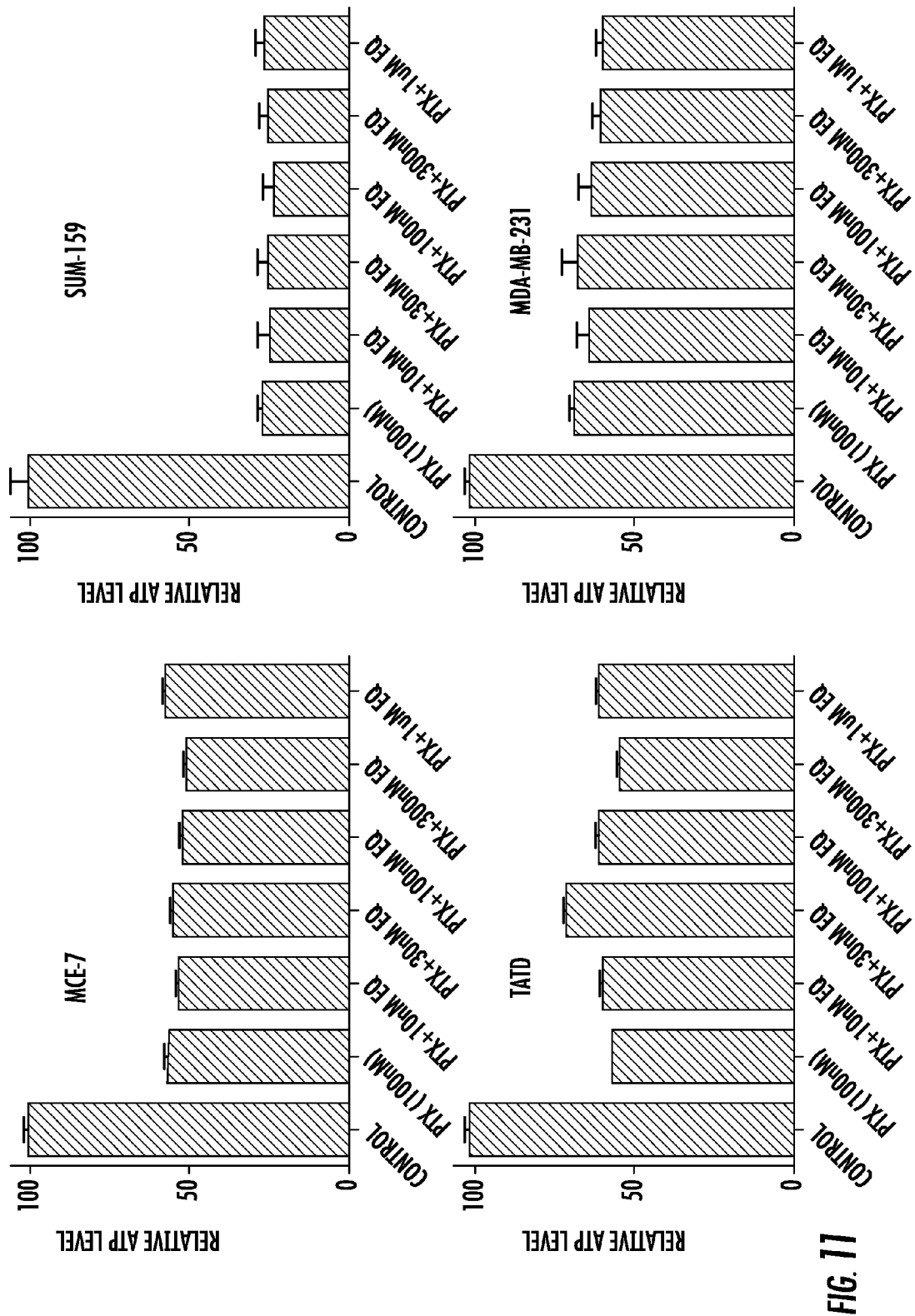

FIG. 2A demonstrates that in a DRG neuronal cell line, 50B11 cells were differentiated, then exposed to paclitaxel (PTX) with or without various concentrations of EQ. ATP levels were measured after 24 hours. EQ provided neuroprotection against PTX neurotoxicity starting at 30 nM concentration;

FIG. 2B demonstrates that primary DRG neurons were grown in culture and allowed to extend their axons for 24 hours. They, they were exposed to PTX or EQ for another 24 hours. Cells were fixed, stained with βIII-tubulin and axon lengths were measured. EQ partially prevented distal axonal degeneration induced by PTX;

FIG. 3 shows the potency of EQ and representative derivatives against paclitaxel neurotoxicity (shown as % neuroprotection; NP) by measuring ATP levels;

FIG. 4 shows the neuroprotection of EQ against paclitaxel neurotoxicity in a mouse model by measuring sensory nerve action potential (SNAP) amplitudes;

FIG. 5 shows the neuroprotection of EQ and EQ Derivative 7 (EQ-7) against paclitaxel neurotoxicity in a mouse model by measuring thermal hypoalgesia;

FIG. 6 shows the protection of EQ and EQ Derivative 7 (EQ-7) of distal axonal degeneration and reduction in intraepidermal nerve fiber density against paclitaxel in the footpads of mice;

FIG. 7 shows an assay to determine the binding efficiency of EQ to recombinant heat shock protein 90 (hsp90), $K_d$ of 280 nM, using a fluorescence quenching method;

FIG. 8 shows the neuroprotection by EQ in DRG neuronal cells in the presence (white bars) and absence (gray bars) of hsp90 siRNA. Downregulation of hsp90 by siRNA reverses neuroprotection by EQ. DRG neuronal cells were cultured for three days with hsp90 siRNA or control siRNA, reduction in hsp90 levels were confirmed and then cells were exposed to paclitaxel with or without EQ;

FIG. 9 demonstrates that EQ does not alter the ATPase activity of hsp90 across a wide dose range;

FIG. 10 demonstrates that EQ does not alter the binding efficacy of paclitaxel to hsp90; and FIG. 11 demonstrates that EQ does not prevent antineoplastic activity of paclitaxel against four different human breast cancer cell lines: MCE-7, SUM-159, TATD, and MDA-MB-231. Paclitaxel had varying degrees of efficacy against four different breast cancer cell lines reducing cell viability by 35% to 75% when cultured alone. When paclitaxel was co-administered with varying concentrations of EQ, no significant change in reduced cell viability was observed.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Ethoxyquin and Derivatives for Treating Peripheral Neuropathies and Other Neurodegenerative Disorders Peripheral neuropathies are a group of neurodegenerative disorders affecting the peripheral nerves and can be caused by various underlying illnesses. Currently, no effective therapy for preventing nerve degeneration exists, except in cases of autoimmune peripheral neuropathies. A non-biased, in vitro assay was developed to screen for compounds that prevented neuronal toxicity of paclitaxel (PTX), capsaicin, and dideoxycytidine (ddC). Ethoxyquin (EQ) was identified as a potential neuroprotective compound. Accordingly, in some embodiments, the presently disclosed subject matter provides compounds, i.e., ethoxyquin (EQ) and representative derivatives, which prevent nerve degeneration in peripheral neuropathies and other neurodegenerative diseases including, but not limited to, chemotherapy-induced peripheral neuropathy (CIPN), diabetic peripheral neuropathy (DPN), human immunodeficiency associated sensory neuropathy (HIV-SN), and amyotrophic lateral sclerosis (ALS).

A. Method for Treating or Preventing Neurodegenerative Disorders

More particularly, in some embodiments, the presently disclosed subject matter provides a method for treating, inhibiting, delaying, or preventing a neurodegenerative disorder in a subject, the method comprising administering to the subject a therapeutically effective amount of a compound of Formula (I) or Formula (II):

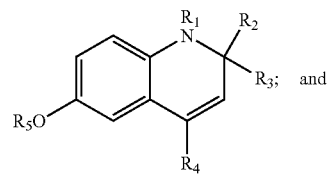

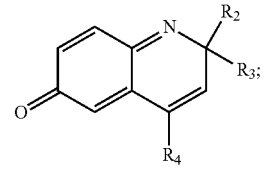

wherein:

$R_1$ is selected from the group consisting of H, substituted or unsubstituted alkyl, and —C(=O)—$R_6$, wherein $R_6$ is substituted or unsubstituted alkyl;

$R_2$, $R_3$, and $R_4$ are each independently substituted or unsubstituted alkyl; and $R_5$ is selected from the group consisting of H, substituted or unsubstituted alkyl, and —C(=O)—$R_6$; or a pharmaceutically acceptable salt thereof.

In particular embodiments, the compound of Formula (I) or Formula (II) is selected from the group consisting of:

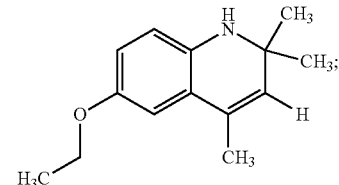

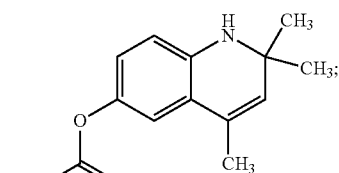

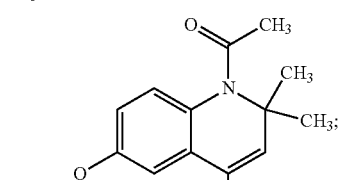

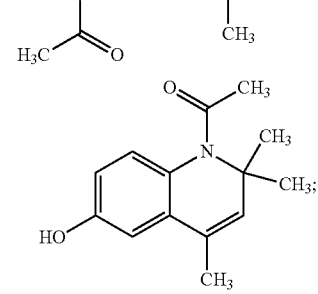

-continued

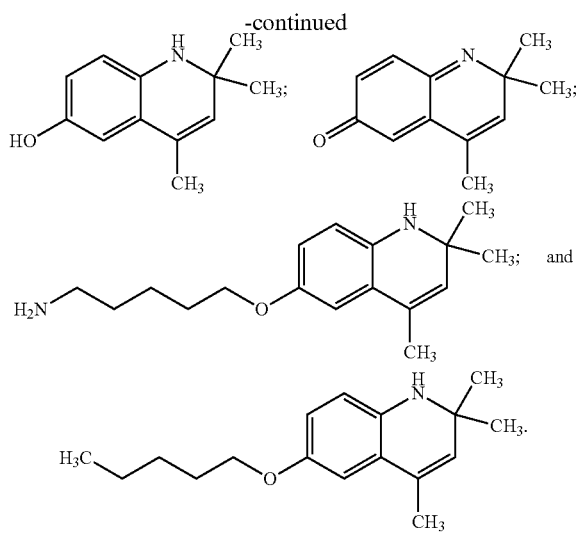

In yet more particular embodiments, the compound of Formula (I) is:

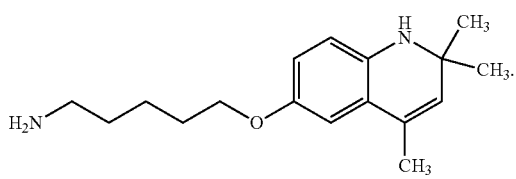 [SMILES: CC1=CC(C)(C)Nc2ccc(OCCCCCN)cc21]

In some embodiments, the neurodegenerative disorder comprises a peripheral neuropathy. In particular embodiments, the peripheral neuropathy is selected from the group consisting of a chemotherapy-induced peripheral neuropathy, a diabetes-induced peripheral neuropathy, an HIV-associated peripheral neuropathy, an idiopathic peripheral neuropathy, an alcohol-induced peripheral neuropathy, and a drug-induced peripheral neuropathy.

In other embodiments, the neurodegenerative disorder is of the central nervous system. In some embodiments, the neurodegenerative disorder is selected from the group consisting of Alzheimer's disease, and Parkinson's disease.

In yet other embodiments, the neurodegenerative disorder comprises a motor neuron disease. In some embodiments, the motor neuron disease is amyotrophic lateral sclerosis (ALS).

In some embodiments, the treating, inhibiting, delaying, or preventing a neurodegenerative disorder in a subject further comprises preventing or partially preventing distal axonal degeneration of a neuron in the subject. In particular embodiments, the distal axonal degeneration is caused by a stress that can result in a neurodegenerative disorder. In yet more particular embodiments, the stress is a chemotherapeutic drug. In certain embodiments, the chemotherapeutic drug is paclitaxel.

The presently disclosed methods generally include contacting at least one cell with at least one compound. The methods thus can be practiced in vitro, in vivo, and ex vivo. They accordingly may be practiced, for example, as a research method to identify compounds or to determine the effects of compounds and concentrations of compounds, as a therapeutic method of treating a disease or disorder involving a neurodegenerative disorder, and as a method to prevent a disease or disorder. In embodiments where the method is a method of treating, it can be a method of therapy (e.g., a therapeutic method) in which the amount administered is an amount that is effective for reducing or eliminating a disease or disorder. In embodiments where the method is a method of prevention, the amount is an amount sufficient to prevent the disease or disorder from occurring or sufficient to reduce the severity of the disease or disorder if it does occur.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compositions can be administered prophylactically to prevent or reduce the incidence or recurrence of the disease, disorder, or condition.

As used herein, the term "inhibiting," and grammatical derivations thereof, refers to the ability of an agent to block, partially block, interfere, decrease, reduce or deactivate an activity, pathway, or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%. In some embodiments, the decrease is a substantial decrease. A substantial decrease means a change of approximately of at least 20% from normal activity, more preferably a change of at least 40%, and even more preferably a change of at least 60%.

By the term "decrease" is meant to inhibit, suppress, attenuate, diminish, arrest, or stabilize a symptom of a neurodegenerative disease, disorder, or condition. It will be appreciated that, although not precluded, treating a disease, disorder or condition does not require that the disease, disorder, condition or symptoms associated therewith be completely eliminated.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The presently disclosed subject matter encompasses a wide variety of neurodegenerative disorders. A "neurodegenerative disorder" is a disorder that is characterized by the progressive loss of the structure or function of neurons. In some embodiments, the neurodegenerative disorder is a peripheral neuropathy and may be selected from the group consisting of chemotherapy-induced, diabetes-induced, HIV-associated, idiopathic, alcohol-induced, and drug-induced. In other embodiments, the neurodegenerative disorder is a disorder of the central nervous system, such as Alzheimer's disease, and Parkinson's disease. In still other embodiments, the neurodegenerative disorder is a motor neuron disease, such as amyotrophic lateral sclerosis (ALS).

More than one compound can be administered at one time, depending on the subject, the characteristics of the compounds, the disease or disorder, and the like. In general, the "effective amount" of a therapeutic agent refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

In general, a dosing of about 0.01 ng to about 1 g, such as about 0.05 ng, 0.5 ng, 1 ng, 50 ng, 100 ng, 500 ng, 1 µg, 5 µg, 10 µg, 50 µg, 100 µg, 500 µg, 50 mg, 100 mg, 500 mg or 1 g per administration should be effective in providing the desired therapeutic or prophylactic result. The exact dosage will depend upon the route of administration, the form in which the compound is administered, the subject to be treated, the body weight of the subject to be treated, the preference and experience of the attending physician, and the like.

By "neuroprotection", it is meant that the compound protects the cell from a stress leading to characteristics of a neurodegenerative disease or disorder or if characteristics of a neurodegenerative disease or disorder are already shown, the compound treats or reduces the effects of the stress in the cell.

By "contacting", it is meant any action that results in at least one molecule of one of the presently disclosed compounds physically contacting at least one cell. It thus may comprise exposing the cell(s) to the compound in an amount sufficient to result in contact of at least one molecule of compound with at least one cell. The method can be practiced in vitro or ex vivo, by introducing, and preferably mixing, the compound and cells in a controlled environment, such as a culture dish or tube. The method can be practiced in vivo, in which case contacting means exposing at least one cell in a subject to at least one molecule of compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s).

B. Method for Modulating an Overall Activity of Heat Shock Protein 90

In another embodiment, the presently disclosed subject matter provides a method of modulating the overall activity of heat shock protein 90 (hsp90). Without wishing to be bound to any one particular theory, it is believed that the chaperone activity of hsp90 is linked to conformation, which in turn is dependent on the binding and release of ATP/ADP (ATPase activity), as well as co-chaperones and client proteins.

By "modulating", it is meant that the activity may increase or decrease. In some embodiments, the modulation of the overall activity of hsp90 is an inhibition of the overall activity of hsp90. In some embodiments, the modulation of hsp90 is determined by the inability of a presently disclosed compound to provide neuroprotection when the overall activity of hsp90 is inhibited.

By "overall activity", it is meant the general activity of a protein which encompasses all of the specific activities of the protein. A specific activity, such as ATPase activity, is a distinct activity of a protein. There may be more than one specific activity that is changed in a protein simultaneously to modulate the overall activity of the protein.

As discussed hereinabove, heat shock proteins may aid in the aberrant behavior of a cell. Hsp90 has been found to assist in the correct functioning of several tumor promoting proteins, such as HER2, EGFR, AKT, and mutant p53, among others. Currently, only agents which inhibit the binding of ATP by targeting the nucleotide binding pocket of hsp90 (ATPase activity) located in the N-terminal domain are being evaluated clinically.

It has been found that the presently disclosed compounds require the presence of hsp90 to provide neuroprotection but they do not alter the ATPase activity of hsp90. In some embodiments, the presently disclosed subject matter provides a method of modulating the overall activity of hsp90 without modulating the ATPase activity of hsp90. Without wishing to be bound to any one particular theory, one hypothesis is that the presently disclosed compounds bind to hsp90 and modify its chaperone activity for one or more important client proteins.

Accordingly, in other embodiments, the presently disclosed subject matter provides a method for modulating the overall activity of heat shock protein 90 (hsp90) without modulating the ATPase activity of hsp90 in a cell, the method comprising contacting the cell with a compound of Formula (I) or Formula (II):

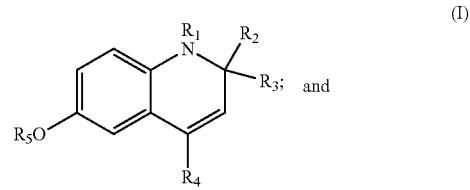

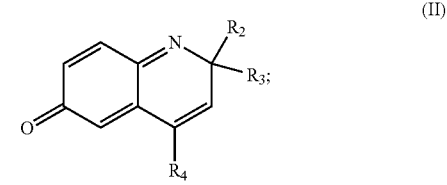

wherein:

R₁ is selected from the group consisting of H, substituted or unsubstituted alkyl, and —C(=O)—R₆, wherein R₆ is substituted or unsubstituted alkyl;

R₂, R₃, and R₄ are each independently substituted or unsubstituted alkyl; and

R₅ is selected from the group consisting of H, substituted or unsubstituted alkyl, and —C(=O)—R₆; or a pharmaceutically acceptable salt thereof;

in an amount sufficient to modulate the overall activity of hsp90 but not modulate the ATPase activity of hsp90.

In particular embodiments, the compound of Formula (I) or Formula (II) is selected from the group consisting of:

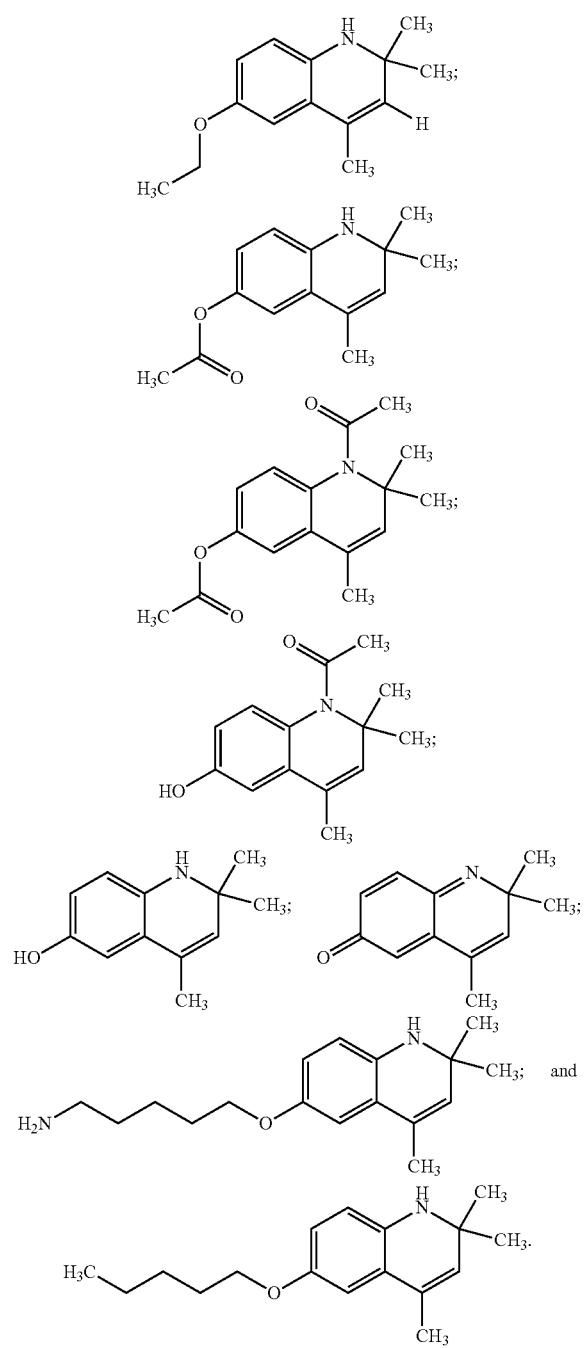

In yet more particular embodiments, the compound of Formula (I) is:

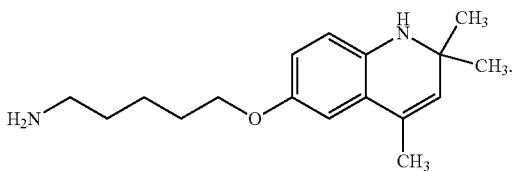

In some embodiments, the modulation of the overall activity of hsp90 is determined by the inability of the compound of Formula (I) or Formula (II) to provide neuroprotection when hsp90 is inhibited.

In particular embodiments, the cell is a dorsal root ganglia (DRG) cell. The cell used in these methods may be any cell that contains hsp90. As described hereinabove, the cell may come from a variety of organisms. As an example, the cell may be from a human.

C. Method for Screening for Neuroprotective Compounds

In another embodiment, the presently disclosed subject matter provides methods to screen for neuroprotective compounds. These methods result in novel neuroprotective compounds that modulate the overall activity of hsp90, but do not modulate the ATPase activity of hsp90.

In some embodiments, these methods comprise contacting a cell having hsp90 overall activity with a potential neuroprotective compound, contacting a cell that is inhibited for hsp90 overall activity with the potential neuroprotective compound, adding a stress that can result in a neurodegenerative disorder to each cell, determining if the compound provides neuroprotection of the cell having hsp90 overall activity and does not provide neuroprotection of the cell which is inhibited for hsp90 overall activity, and determining the ATPase activity of hsp90 in the cell having hsp90 overall activity. In these embodiments, the stress is added to the cell after the addition of the potential neuroprotective compound so that the preventative effects of the potential neuroprotective compound can be determined In some embodiments, the stress is added to the cell before the addition of the potential neuroprotective compound so that the method is a method of treating or reducing the effects of the stress in the cell. Thus, these methods comprise adding a stress that can result in a neurodegenerative disorder to a cell with hsp90 overall activity and to a cell that is inhibited for hsp90 overall activity, contacting each cell with a potential neuroprotective compound, determining if the compound provides neuroprotection of the cell with hsp90 overall activity and does not provide neuroprotection of the cell which is inhibited for hsp90 overall activity, and determining the ATPase activity of hsp90 in the cell with hsp90 overall activity.

In some embodiments, before contacting each cell with a potential neuroprotective compound or adding a stress to each cell, an in vitro assay may be performed to determine if the potential compound is capable of binding to hps90. In some embodiments, a neuroprotective compound may modulate the overall activity of hsp90 without directly binding to it and therefore, this step is an optional step to screen for neuroprotective compounds that directly bind to hsp90. Those of skill in the art are well aware of, and fully capable of selecting and executing, appropriate in vitro binding assays. Examples include, but are not limited to, immunohistochemical assays, Western blot analyses, ELISAs, and affinity columns The cells used in these methods of developing novel neuroprotective compounds may be any cell, human or nonhuman, that contains hsp90. In some embodiments, the cell is a dorsal root ganglia cell.

The stress that can be used to determine if a potential compound provides neuroprotection to the cell can be any stress that is known to be involved in neurodegenerative disorders or that affects heat shock proteins. In some embodiments, the stress is a chemotherapy drug, such as paclitaxel, since it has been shown that peripheral neuropathy is a common side effect of chemotherapy. In other embodiments, the stress is elevated temperature, a virus, a non-chemotherapy drug, alcohol, and the like. In some embodiments, the methods comprise more than one stress added to the cells simultaneously.

II. Novel Compounds

In yet other embodiments, the presently disclosed subject matter provides a compound of the formula:

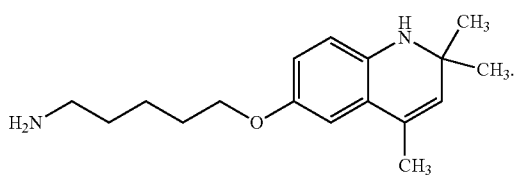 [SMILES: CC1=CC(C)(C)Nc2ccc(OCCCCCN)cc21]

In yet more particular embodiments, the compound comprises a chloride salt:

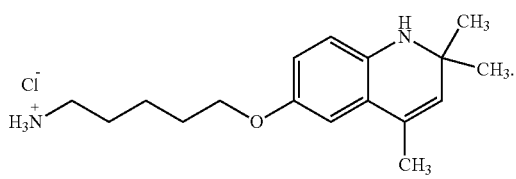 [SMILES: Cl ; CC1=CC(C)(C)Nc2ccc(OCCCCCN)cc21]

The presently disclosed subject matter also provides kits. In general, the kits comprise a sufficient amount of at least one compound having a neuroprotective capacity, such as the compounds described herein, to cause inhibition, delay, or prevention of a neurodegenerative disorder. Typically, the compound will be supplied in one or more container, each container containing a sufficient amount of compound for at least one dosing of the patient. The kits can comprise other components, such as some or all of the components necessary to practice a method of the presently disclosed subject matter. The kits may contain a syringe for administering a dose of the compound. The kits also may comprise filters for sterilization prior to delivery. They may likewise contain sterile water or buffer for rehydration or reconstitution of dry substance, prior to administration to a patient. In embodiments, multiple doses of compound are provided in the kit, either all in a single container (e.g., a vial) or distributed among two or more containers. Preferably, the kit and its contents are sterile or have been sterilized.

III. Pharamceutical Compositions

In another embodiment, the present disclosure provides a pharmaceutical composition including at least one compound of Formula (I) or Formula (II) alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). As provided in more detail herein below, pharmaceutically acceptable salts include, but are not limited to, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiologically saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the disclosed trioxane sulfur dimer compounds also may be combined with include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

IV. Chemical Difinitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae I-II are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., $—CH_2O—$ is equivalent to $—OCH_2—$; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2 5}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

Each of above terms (e.g., "alkyl," "heteroalkyl," "cycloalkyl", and "heterocycloalkyl," as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein also are meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of Compounds

Chemicals were purchased from Sigma-Aldrich (St. Louis, Mo.) and used without further purification. Solvents were purchased from suppliers as anhydrous grade. NMR spectra were recorded at room temperature on a Bruker-400 MHz spectrometer. Chemical shifts are reported in ppm with TMS as the internal standard.

Derivatives 1, 2, 3 were synthesized as follows: 2,2,4-trimethyl-1,2-dihydro-6-quinolinol (500 mg, 2.5 mmol) and Et$_3$N (243 µL, 3 mmol) were added into freshly distilled THF (15 mL). The resulted solution was stirred for 15 min at 0° C., then acetyl chloride (213 µL, 3 mmol) was slowly added during a 15 min period. The reaction mixture was continued to stir for 30 minutes at 0° C. under argon, then overnight at room temperature. The solvent was evaporated under vacuum. The residue was extracted with 2N NaOH and CH$_2$Cl$_2$, and then passed through Na$_2$SO$_4$. The crude product was purified via flash chromatography with CH$_2$Cl$_2$ to MeOH: CH$_2$Cl$_2$ (2:98) as eluent. Derivative 1 (160 mg, 30%), derivative 2 (96 mg, 16%) and derivative 3 (134 mg, 25%) were obtained as yellow oils at different elution times. $^1$H NMR (CDCl$_3$-d$_6$): Derivative 1: 2.28 (3H, s); derivative 2: 2.35 (3H, S), 2.16 (3H, s); derivative 3: 2.04 (3H, s).

Derivative 4 was commercially available from Chem-Bridge Corporation (San Diego, Calif.).

Derivative 5 was synthesized according to Taimr et al., Antioxidants and stabilizers, CXIII Oxidation products of the antidegradant ethoxyquin. Die Angewandte Makromolekulare Chemie 1991, 190, 53-65.

Boc-Derivative 6 was synthesized as follows: To a solution of 2,2,4-trimethyl-1,2-dihydro-6-quinolinol (148 mg, 0.78 mmol) in freshly distilled acetone (5 mL), were added anhydrous K$_2$CO$_3$ (130 mg, 0.94 mmol) and 5-(t-Boc-amino)-1-pentyl bromide (250 mg, 0.94 mmol). The obtained mixture was refluxed overnight. Solvent was evaporated under vacuum, and solid residue was dissolved with 2N NaOH and extracted with ethyl acetate three times. The combined organic layer was dried under vacuum. The crude product was prepurified via flash chromatography with CH$_2$Cl$_2$ as eluent, followed by further purification using HPLC with a Thermo Betasil C18 reverse phase column. Boc-Derivative 6 (40 mg, 0.117 mmol) was obtained as brown oil in a 15% yield. $^1$H NMR (CDCl$_3$, 400 MHz) δ 7.357 (d, 1H), 6.902 (s, 1H), 6.801 (d, 1H), 5.672 (5, 1H), 3.985 (t, 2H), 3.165 (t, 2H), 2.094 (s, 3H), 1.904-1.775 (m, 2H), 1.665-1.553 (m, 2H), 1.507 (s, 9H), 1.470 (s, 6H), 1.334-1.247 (m, 2H). $^{13}$C NMR (CDCl$_3$, 100 MHz) δ 160.894, 159.773, 130.498, 130.062, 129.347, 123.741, 120.365, 112.914, 111.789, 68.104, 62.908, 56.189, 40.160, 29.818, 28.645, 28.369, 24.412, 23.098, 18.118.

Derivative 6 was synthesized as follows: Boc-Derivative 6 (40 mg, 0.117 mmol) was dissolved in CH$_2$Cl$_2$ (3 mL), and TFA (3 mL) was added dropwise to this solution. After stirring for 2 h, the volatile materials were removed under reduced pressure. The residue was separated by flash chromatography on silica gel with 99:5 of CH$_2$Cl$_2$: MeOH as eluent. Derivative 6 (28 mg, 0.1 mmol) was obtained as yellow oil in 85% yield. $^1$H NMR (CDCl$_3$, 400 MHz) δ 8.126 (s, 2H), 7.194 (d, 1H), 6.817 (s, 1H), 6.758 (d, 1H), 5.584 (s, 1H), 3.965 (t, 2H), 2.911 (s, 1H), 2.598 (q, 2H), 2.046 (s, 3H), 1.895-1.679 (m, 2H), 1.611-1.494 (m, 2H), 1.412 (s, 6H), 1.353-1.208 (m, 2H). $^{13}$C NMR (CDCl$_3$, 100 MHz) δ 161.483, 134.809, 134.253, 132.239, 125.459, 119.248, 118.395, 115.844, 72.495, 58.890, 54.601, 33.097, 31.937, 30.521, 27.686, 23.152.

Derivative 7 was synthesized as follows: To a solution of 2,2,4-trimethyl-,2-dihydro-6-quinolinol (1 g, 5.29 mmol) in freshly distilled acetone (20 mL) were added anhydrous K$_2$CO$_3$ (732 mg, 5.29 mmol) and diamyl sulfite (1.26 g, 5.29 mmol). The obtained mixture was refluxed overnight. The same workup and purification procedure was used as for Der. 6. Derivative 7 (780 mg, 3.02 mmol) was obtained as light yellow oil in a 57% yield. $^1$H NMR (CDCl$_3$, 400 MHz) δ 10.464 (s, 1H), 7.357 (d, 1H). 6.916 (s, 1H), 6.789 (d, 1H), 5.666 (s, 1H), 3.986 (t, 2H), 2.085 (s, 3H), 1.896-1.786 (m, 2H). 1.499 (s, 6H), 1.451-1.336 (m, 6H), 0.976 (t, 3H), $^{13}$C NMR (CDCl$_3$, 100 MHz) δ160.176, 130.822, 130.089, 128.919, 123.756, 119.945, 113.137, 111.748, 68.450, 56.988, 28.969, 28.239, 23.808, 22.389, 17.903, 13.923.

The chemical structures of EQ and representative derivatives are shown in FIG. 1.

Example 2

Neuroprotection Against Paclitaxel Neurotoxicity in DRG Neuronal Cells

The neuronal protection assay used herein was based on an assay described by Chen et al., 2007. Conditions for culturing the 50B11 cells and measuring the ATP levels were optimized for the 96-well plate format. Briefly, 3500 cells/well in media (Neurobasal medium, 5 µg/mL blasticidin, 10% fetal bovine serum (FBS), 0.5 mM glutamine, 1×B-27 supplement, 0.2% glucose) were plated in 96-well plates for 24 h, then differentiated with 100 µM forskolin (Sigma-Aldrich, St Louis, Mo.) in culture medium with reduced serum (0.2%). Constant concentrations of paclitaxel with or without EQ and representative derivatives were added to the wells for another 24 h. Cellular ATP levels were measured using ViaLight Plus kit (Cambrex, East Rutherford, N.J.) according to manufacturer's protocol on a LMaxl microplat reader (Molecular Devices, Silicon Valley, Calif.). Bars marked with * indicate statistically significant differences with p<0.05.

Measurements of axonal lengths to determine axonal degeneration induced by EQ and representative derivatives were done as described in Keswani et al., "FK506 is neuroprotective in a model of antiretroviral toxic neuropathy," *Annals of Neurology*, 53(1):57-64 (2003). Initially, dorsal root ganglia (DRG) cells were harvested from embryonic rats (14.5 days old) according to standard protocol, then cells were plated onto collagen-coated glass coverslips and allowed to extend axons for 24 h in media (Neurobasal medium, 50 mM PS, 0.2% fetal bovine serum (FBS), 0.5 mM glutamine, 1×B-27 supplement, 0.2% glucose, 10 ng/mL glial cell line-derived neurotrophic factor (GDNF)). Paclitaxel (PTX), EQ and representative derivatives, or vehicle controls were added to the wells for another 24 h incubation. DRG cells were fixed with 4% paraformaldehyde and stained with anti-βIII-tubulin antibody to delineate the axons. Axon lengths were measured in multiple fields using a random sampling method as described by Keswani et al., 2003. All experiments were performed in triplicates and repeated twice. Statistical analysis was done using the ANOVA procedure. Correction for multiple comparisons was completed with Fisher's protected least significant difference. Bars marked with * indicate statistically significant differences with $p<0.05$.

To show that EQ could provide neuroprotection against chemotherapy drugs, the neuronal protection assay and the axonal length assays described above were performed in a rat dorsal root ganglion (DRG) neuronal cell line (50B 11) exposed to PTX (FIG. 2). The neuronal protection assay showed that EQ provided neuroprotection against PTX starting at around 30 nM concentration (FIG. 2A). The axon length assay demonstrated that EQ partially prevented distal axonal degeneration induced by PTX (FIG. 2B).

Various analogues of EQ (Derivatives 1-5, 7) also were examined for their potency in preventing PTX-induced neurotoxicity using the ATP assay (FIG. 3). Most of the EQ derivatives provided potent neuroprotection in the nanomolar range against PTX neurotoxicity. Experiments involving EQ derivatives were conducted in the same way as with EQ.

Example 3

Neuroprotection Against Paclitaxel Neurotoxicity in a Mouse Model

After demonstration that EQ provided neuroprotection in vitro, the use of EQ for preventing PTX induced distal axonal degeneration in a mouse model of chemotherapy induced peripheral neuropathy (CIPN) was examined. In this model, animals develop thermal hypoalgesia and reduction in sensory nerve action potential (SNAP) amplitudes. AJ mice were given three doses of PTX at 25 mg/kg intravenously every other day (days 1, 3 and 5). Vehicle control or EQ was administered daily starting on day 1 and tissues were harvested at day 19. Immediately before tissue harvest, sensory nerve conduction studies and thermal sensation measurements were carried out.

Paclitaxel caused a reduction in SNAP amplitude as recorded in the tail sensory nerves of AJ mice treated with PTX (Paclitaxel only bar; FIG. 4). The EQ compound at various doses prevented this reduction in SNAP amplitude, suggesting that EQ has neuroprotective characteristics in vivo.

Further, thermal hypoalgesia induced by PTX (Paclitaxel only bar) was prevented with various doses of EQ and its derivative, the EQ-7 compound (FIG. 5).

FIG. 6 shows that PTX causes distal axonal degeneration and reduction in intraepidermal nerve fiber density in the footpads of AJ mice treated with PTX (Paclitaxel only bar). This loss of distal axons was prevented in animals given various doses of the EQ or EQ-7 compound.

In addition to these data, it also has been shown that EQ at 75 μg/kg/day prevents distal axonal degeneration seen in a mouse model of HIV-associated sensory neuropathy and reverses distal axonal degeneration seen in diabetic rats (data not shown). Furthermore, autonomic testing in diabetic rats has demonstrated that EQ prevents erectile dysfunction induced by diabetes (data not shown).

Therefore, all of these data combined show that EQ and representative derivatives can provide broad neuroprotection in vitro and in vivo against various forms of neurodegenerative disorders.

Example 4

The Effect of Ethoxyquin on Hsp90

For the binding studies using affinity capture chromatography, the AminoLink Plus Immobilization Kit was used (Thermo Scientific, Logan, Utah). The assay procedure was based on Koul et al., "Diarylquinolines Target Subunit C of Mycobacterial ATP Synthase," *Nature Chemical Biology* 3:323-324 (2007), and the manufacturer's protocol Amino-Link Plus Coupling resin was incubated overnight in a solution of 200 mmol EQ-derivative 6 (DMSO; pH 7.2 Coupling buffer/20:80). Then the resin was equilibrated to pH 7.2 in phosphate buffer containing 150 mM NaCl. To characterize the compound linked to AminoLink, HPLC was used to measure the coupling efficiency. Residue and uncoupled compound in solution were determined and the amount of coupled fraction was calculated (data not shown). Resins were treated with 50 mM sodium cyanoborohydride solution (40 μL in 2 mL quenching buffer) to block the residual active sites on the resin surface. After several washing steps, total protein extracts from the 50B-11 cell line and the DRG cell line (obtained in 20 g mice by unilateral excision of the L3, L4, L5, and L6 dorsal root ganglia) were passed through these affinity columns and extensively washed to remove non-specifically bound proteins. Elution was performed with 1 mM EQ-derivative 6 in elution buffer. The elute was resolved by SDS-PAGE and then revealed by Pierce SilversStain and Coomassie Brilliant Blue. Selected bands of gel were cut and measured by MALDI-TOF Mass Spectrometry. Proteins were searched and identified in a protein database and then analyzed on the Scaffold 3 proteome software.

For experiments involving the analysis of changes in gene expression using reverse transcription (RT)-PCR, the assay procedure was based on Chen et al., 2007. 50B11 cells were grown in media (Neurobasal medium, 5 μg/mL blasticidin, 10% fetal bovine serum (FBS), 0.5 mM glutamine, 1×B-27 supplement, 0.2% glucose) containing 100 μM forskolin for 12 h. Constant concentrations of paclitaxel (PTX) with or without EQ were added to the wells for the appropriate time in culture medium with forskolin (50 μM) and reduced serum (0.2%). Total RNA was extracted using the TR1zol Reagent (Invitrogen, Life Technologies, Carlsbad, Calif.) according to standard protocols. Using the Ready-To-Go You-Prime First-Strand Bead (Amersham Biosciences, GE Healthcare, Buckinghamshire, England), 2 μg total RNA was reverse transcribed according to manufacturer's protocols. Measurements of mRNA levels were performed by real-time RT-PCR in a DNA Engine Opticon Continuous Fluorescence Detection System with DyNAmo SYBR Green Polymerase (MJ Research, St. Bruno, Canada). GAPDH was used as an internal control gene. All primers were designed using the individual gene sequences in the GenBank and EMBL nucleotide sequence database on Primer3 and synthesized by Integrated DNA Technologies Inc (Coralville, Iowa). To achieve specificity and maximum efficiency, the binding positions of all primers were chosen to produce amplicons of 90-120 bp, and gel electrophoresis was carried out to confirm the correct size of the primers and the absence of nonspecific bands. The comparative CT method was used to calculate the expression levels of individual genes before and after treatment (Hoke et al., "Schwann Cells Express Motor and Sensory Phenotypes That Regulate Axon Regeneration," *J. Neurosci.* 26(38): 9646-9655 (2006)).

For the RNA inhibition experiments, transfection with siRNA was carried out according to the manufacturer's protocol. 50B11 cells were plated in 6-well plates in culture medium (Neurobasal medium, 10% fetal bovine serum (FBS), 0.5 mM glutamine, 1×B-27 supplement, 0.2% glucose) without antibiotics overnight and allowed to reach 50-70% confluence. On the second day, 1 μL siRNA oligomer (Ambion, Life Technologies, Carlsbad, Calif.) was diluted in 250 μL Opti-MEM media, and 5 μL Lipofectation 2000 (Invitrogen, Life Technologies, Carlsbad, Calif.) in another 250 μL Opti-MEM media. After 5 minutes incubation, dilutions were combined and incubated for 20 minutes at RT and then the oligomer-Lipofectation 2000 complexes were added to each well. After the addition of 1.5 mL Opti-MEM media, the resulted media was mixed gently. After four hours after the transfection, the culture medium was replaced by culture medium containing blasticidin (5 μg/mL), and cells were grown in this medium for 72 hours.

The protein isolation, protein electrophoresis (SDS-PAGE) and Western blotting assays were performed according to the instructions of the manufacturer. Total protein was extracted from 50B11 cells using M-PER® Mammalian Protein Extraction Reagent (Invitrogen, Life Technologies, Carlsbad, Calif.) in the presence of protease inhibitor (Thermo Scientific, Logan, Utah). The measurements of total protein concentrations were performed using BCA kits (Thermo Scientific, Logan, Utah) on SpectraMax 340PC microplate reader (Molecular Devices, Palo Alto, Calif.). Samples (30 μg of total protein per well) and standards (SeeBlue® Plus2 Pre-Stained Standard, Invitrogen, Life Technologies, Carlsbad, Calif.) were loaded onto the wells (Ready Gel® 4-15% Tris-HCl, 50 μL$^{-1}$ gel; Bio-Rad, Hercules, Calif.). The gel was run at 100V for 1.5 h, and then transferred to PVDF membrane (Bio-Rad, Hercules, Calif.) according to the manufacturer's protocol. The membrane was blocked at room temperature for 1 h in blocking buffer (5% milk), and then incubated with primary antibody (Abcam, Cambridge, Mass.; StressMarq, BC, Canada) at a 1:1000 dilution overnight at 4° C. This step was followed by three washes and incubation with a second antibody at 1:1000 dilution at room temperature for 1 h. After three washes and development in ECL™ Western Blotting Detection Reagents (GE-Healthcare, UK), the membrane was covered in transparent wrap and exposed to X-ray film according to the manufacturer's recommendation.

For the fluorescence-quenching assay, fluorescence intensity was recorded on a SpectraMax Gemini XS plate reader (Molecular Devices, Palo Alto, Calif.) using a 96-well black PCR plate (Thermo Scientific, Logan, Utah). Compounds (10 mM in ethanol) were diluted with 50 mM Tris-HCl (pH 7.4) to obtain a solution with a 15 μM final concentration. Aliquots of proteins were added to the compounds solution and mixed with micro pipette by gently pulling in and drawing out the solution. Fluorescence intensities ($\lambda_{ex}$=350 nm, $\lambda_{em}$=450 nm) were measured at 25° C. Equilibrium dissociation constant KD was obtained by fitting the data using the nonlinear least squares option of the GraphPad Prism software. All experiments were completed in duplicates and repeated at least three times.

The assay procedure for the colorimetric determination of ATPase activity was based on Rowlands et al., "High-throughput Screening Assay for Inhibitors of Heat-Shock Protein 90 ATPase Activity," *Analytical Biochemistry* 327: 176-183 (2004). The malachite green reagent was prepared on the day of use. It contained malachite green (Sigma Aldrich, St. Louis, Mo.; 0.0812%, w/v), polyvinyl alcohol (Sigma Aldrich, St. Louis, Mo.; 2.32%, w/v), ammonium molybdate (Sigma Aldrich, St. Louis, Mo.; 5.72%, w/v, in 6 M HCl), and UltraPure Distilled Water (Invitrogen, Life Technologies, Carlsbad, Calif.), mixed in the ratio 2:1:1:2. The reagent was initially dark brown, and then it changed to a golden yellow after 2 h at room temperature, which meant it was ready for use. The assay buffer (pH 7.4) was 100 mM Tris-HCl, 20 mM KCl, 6 mM $MgCl_2$.

The test compounds were dissolved in 100% (v/v) DMSO to give a stock concentration of 10 mM. This solution was diluted to six appropriate concentrations with test compounds in the assay buffer. 5 μL of each compound solution was added to each well of the Perkin-Elmer 96-well assay plate. The first two rows of the 96-well plate contained DMSO only, representing the control and background values, respectively. ATP (Sigma Aldrich, St. Louis, Mo.) was dissolved in the assay buffer to make a stock solution with a concentration of 2.5 mM, which was placed on ice. A 10 μL ATP solution was added to each well to give a final assay concentration of 1 mM. Just before use, hsp90 protein (StressMarq Biosciences, British Columbia, Canada) was kept on ice and suspended in cold assay buffer to make a stock solution with a concentration of 0.50 mg/mL. 10 μL of the stock HSP90 solution was added to each well (except for the background wells that received 10 μL of assay buffer), giving a final assay volume of 25 μL. The absorbance at 620 nm was measured using the SpectraMAX 340PC microplate reader (Molecular Devices, Palo Alto, Calif.). All experiments were performed in duplicate and repeated at least twice.

To help identify the mechanism of action by which EQ provides neuroprotection of neurodegenerative disorders, an EQ-derivative, EQ-derivative 6, was made and bound to the column described above. DRG lysates were passed through the column and the eight proteins that bound to the column were collected. RNA inhibition was used to individually downregulate the levels of each protein that bound to EQ and the reduction in protein levels was validated by Western blotting. It was then determined if neuroprotection by EQ was lost when each protein was down-regulated.

The effect of RNA inhibition for one of the proteins, hsp90, is shown in FIG. 8. DRG neuron cells were cultured for three days with hsp90 siRNA or control siRNA, the reduction in hsp90 levels in the samples with hsp90 siRNA was confirmed, and the cells were then exposed to paclitaxel with or without EQ. Neuroprotection by EQ can be seen when comparing the PTX (−) siRNA sample to the PTX+ 100 nM EQ (−) siRNA sample. In the samples with hsp90 siRNA included, the neuroprotection by EQ disappeared as seen by the PTX (+) siRNA sample compared to the PTX+ 100 nM EQ (+) siRNA sample. These studies identified that when hsp90 was downregulated by RNA inhibition, neuroprotection provided by EQ was prevented.

To determine the binding efficiency, fluorescence quenching experiments were carried out with recombinant hsp90. It was determined that EQ binds to recombinant hsp90 with a $K_d$ of 280 nM (FIG. 7).

To determine the effect of EQ on the ATPase activity of hsp90 as traditional hsp90 ATPase inhibitors have been shown to have anti-cancer efficacy, the ATPase activity of hsp90 was measured over a wide dose range of EQ. It was determined that EQ does not affect the ATPase activity of hsp90 (FIG. 9).

Further, it was known that paclitaxel binds to hsp90. To determine if EQ was binding to the same site and displacing paclitaxel, the binding efficacy of paclitaxel to hsp90 was measured. It was found that EQ did not affect the binding of paclitaxel to hsp90 suggesting that EQ and paclitaxel bind to different sites on hsp90 (FIG. 10). Without wishing to be bound to any one particular theory, since hsp90 was required for EQ's neuroprotection, the data herein suggests that EQ modifies a yet unknown activity of hsp90. It is possible that EQ binds to hsp90 and modifies its chaperone activity for an important client protein.

The data provided herein shows that the modulation of hsp90 overall activity, but not its ATPase activity, is a molecular target for the development of novel neuroprotective compounds.

Example 5

The Effect of the EQ Compound on the Antineoplastic Activity of Paclitaxel in Human Breast Cancer Cells To determine the effect of EQ on the antineoplastic activity of paclitaxel, the conditions for culturing four cancer cell lines and measuring the ATP levels were optimized for the 96-well plate format. Briefly, 1500 cells/well in media (MDA-MB-231 in DMEM with 10% FBS; MCF-7 in DMEM with 10% FBS; TATD in RPMI with 10% FBS; SUM159 in DMEM/F-12 (250 mL/250 mL) with 5% FBS, 500 µL of 10 mg/mL insulin and 25 µL of 10 mg/mL hydrocordisol) were plated in 96-well plates for 24 h. Constant concentrations of paclitaxel (PTX) with or without EQ were added to the wells for another 24 h. Cellular ATP levels were measured using ViaLight Plus kit (Cambrex) according to the manufacturer's protocol on a LMaxI microplate reader (Molecular Devices, Palo Alto, Calif.).

For EQ to be clinically useful, it was preferable that it not alter the anti-cancer properties of paclitaxel. To determine if EQ affected the anti-cancer properties of paclitaxel, the antineoplastic activity of paclitaxel was assayed in four different breast cancer cell lines (MCE-7, MDA-MB-231, TATD and SUM-159) in the presence of EQ. It was found that EQ did not affect the ability of paclitaxel to reduce cell viability in any of the four breast cancer cell lines tested as seen by relative ATP levels when varying concentrations of EQ were added to each cell line (FIG. 11).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Chen, W.; Mi, R.; Haughey, N.; Oz, M; Hoke, A , "Immortalization and characterization of a nociceptive dorsal root ganglion sensory neuronal line," *J. Peripher. Nerv. Syst.* 12(2), 121-130 (2007);

Koul et al., "Diarylquinolines Target Subunit C of Mycobacterial ATP Synthase," *Nature Chemical Biology* 3:323-324 (2007);

Hoke et al., "Schwann Cells Express Motor and Sensory Phenotypes That Regulate Axon Regeneration," *J. Neurosci.* 26(38):9646-9655 (2006);

Keswani et al., "FK506 is neuroprotective in a model of antiretroviral toxic neuropathy," *Annals of Neurology*, 53(1): 57-64 (2003);

Rowlands et al., "High-throughput Screening Assay for Inhibitors of Heat-Shock Protein 90 ATPase Activity," *Analytical Biochemistry* 327:176-183 (2004);

Taimr, L.; Prusikova, M.; Pospisil, J., "Antioxidants and stabilizers, CXIII Oxidation products of the antidegradant ethoxyquin," *Die Angewandte Makromolekulare Chemie* 190: 53-65 (1991).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for modulating the chaperone activity of heat shock protein 90 (hsp90) without modulating the ATPase domain activity of hsp90 in a cell, the method comprising contacting the cell with the compound:

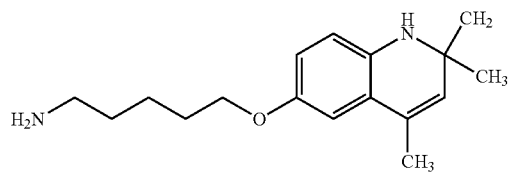 [SMILES: CC1=CC(C)(C)Nc2ccc(OCCCCCN)cc21]

or a pharmaceutically acceptable salt thereof;
in an amount sufficient to modulate the chaperone activity of hsp90 but not modulate the ATPase domain activity of hsp90.

2. A compound of the formula: